(12) United States Patent
Hornbaek et al.

(10) Patent No.: US 10,226,491 B2
(45) Date of Patent: Mar. 12, 2019

(54) SYNERGISTIC ANTIMICROBIAL EFFECT

(75) Inventors: Tina Hornbaek, Birkeroed (DK);
Maike Lisberg, Espergaerde (DK);
Silja Kej Diemer, Frederiksberg (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 14/110,388

(22) PCT Filed: Apr. 9, 2012

(86) PCT No.: PCT/EP2012/056384
§ 371 (c)(1),
(2), (4) Date: Dec. 20, 2013

(87) PCT Pub. No.: WO2012/136830
PCT Pub. Date: Oct. 11, 2012

(65) Prior Publication Data
US 2014/0093487 A1    Apr. 3, 2014

(30) Foreign Application Priority Data

Apr. 8, 2011    (EP) .................................... 11161609

(51) Int. Cl.
*A61K 35/747* (2015.01)
*A01N 63/00* (2006.01)
*A23C 9/123* (2006.01)
*C12R 1/225* (2006.01)

(52) U.S. Cl.
CPC ............ *A61K 35/747* (2013.01); *A01N 63/00* (2013.01); *A23C 9/1234* (2013.01); *C12R 1/225* (2013.01)

(58) Field of Classification Search
None
See application file for complete search history.

(56) References Cited

U.S. PATENT DOCUMENTS

| | | | |
|---|---|---|---|
| 5,378,458 A | 1/1995 | Mayra-Makinen et al. |
| 5,965,414 A | 10/1999 | Vandenbergh et al. |
| 10,059,919 B2 | 8/2018 | Hornbaek et al. |
| 2005/0095318 A1 | 5/2005 | Schwenninger et al. |

(Continued)

FOREIGN PATENT DOCUMENTS

| CN | 101613667 A | 12/2009 |
|---|---|---|
| EP | 0 221 499 A2 | 5/1987 |

(Continued)

OTHER PUBLICATIONS

Danisco A/S, "HOLDBAC-TM YM Protective Cultures", Danisco A/S , 2008, pp. 1-4, www.foodnavigator.com/content/ . . . /Daniscocultures-FN-wk14-2008.pdf.

(Continued)

*Primary Examiner* — Erin M. Bowers
(74) *Attorney, Agent, or Firm* — Foley & Lardner LLP

(57) ABSTRACT

The present invention is related to the field of bioprotection, in particular to an antimicrobial composition comprising a *Lactobacillus rhamnosus* strain and/or a *Lactobacillus paracasei* strain. Furthermore, the present invention concerns uses for such an antimicrobial composition, food, feed and pharmaceutical products comprising such an antimicrobial composition, a method of manufacturing such food, feed and pharmaceutical products and a method for reducing the content of unwanted microorganisms of such food, feed and pharmaceutical products.

15 Claims, 7 Drawing Sheets

(56) References Cited

U.S. PATENT DOCUMENTS

| | | |
|---|---|---|
| 2005/0271640 A1 | 12/2005 | Suomalainen et al. |
| 2008/0107699 A1 | 5/2008 | Spigelman et al. |
| 2011/0045134 A1 | 2/2011 | Perrier et al. |
| 2015/0079057 A1 | 3/2015 | Hornbaek et al. |

FOREIGN PATENT DOCUMENTS

| | | |
|---|---|---|
| EP | 0 302 300 A2 | 2/1989 |
| EP | 0 576 780 A2 | 1/1994 |
| EP | 0 852 114 A1 | 7/1998 |
| EP | 0852114 * | 7/1998 |
| EP | 1 308 506 A1 | 5/2003 |
| EP | 1 992 351 | 11/2008 |
| EP | 1 116 1609.0 | 4/2011 |
| JP | 2011-505162 A | 2/2011 |
| WO | WO-03/070203 A1 | 8/2003 |
| WO | WO-03/070260 A1 | 8/2003 |
| WO | WO-2004/041305 A1 | 5/2004 |
| WO | WO-2007/140621 A1 | 12/2007 |
| WO | WO-2009/098411 A2 | 8/2009 |
| WO | WO-2012/136830 A1 | 10/2012 |

OTHER PUBLICATIONS

EP Application No. 111616109.0, Search Report dated Jul. 14, 2011.
EP Application No. 12163508.0, Search Report dated Sep. 10, 2012.
EP Application No. 12163509.8, Search Report dated Sep. 10, 2012.
EP Application No. 12168971.5, Search Report dated Nov. 22, 2012.
EP Application No. 12168977.2, Search Report dated Jun. 28, 2012.
Hassan et al., "Antifungal activity of Lactobacillus paracasei ssp. tolerans isolated from a sourdough bread culture", International Journal of Food Microbiology, Elsevier Science Publishers, Amsterdam, NL, vol. 121, No. 1, pp. 112-115 2008, Accepted Nov. 2, 2007.
Kosikowski, F.V. et al., "Cheese and Fermented Milk Foods", 1997, 3rd Ed. F.V. Kosikowski, L.L.C. Westport, PCT, pp. 109-126, vol. 1, chapter 7.
PCT/EP2012/0536384, International Preliminary Report on Patentability dated Oct. 8, 2013.
PCT/EP2012/056384, International Search Report dated May 7, 2012.
PCT/EP2013/057400, International Search Report dated May 22, 2013.
PCT/EP2013/057410, International Search Report dated May 22, 2013.
Schnurer J et al, "Antifungal lactic acid bacteria as biopreservatives", Trends in Food Science and Technology, vol. 16, No. 1-3, Jan. 1, 2005.
Schwenninger SM et al., "A Mixed Culture of Propionibacterium jensenii and Lactobacillus paracasei subsp. paracasei Inhibits Food Spoilage Yeasts", Systematic and Applied Microbiology, vol. 27, No. 2, Jan. 1, 2004.
Schwenninger SM, "Detection of antifungal properties in Lactobacillus paracasei subsp. paracasei SM20, SM29, and SM63 and molecular typing of the strains", Journal of Food Protection, vol. 68, No. 1, Jan. 1, 2005.
Tharmaraj, N. et al., "Antimicrobial effects of probiotic bacteria against selected species of yeasts and moulds in cheese-based dips", International Journal of Food Science & Technology, (2009), Accepted in revised form Apr. 8, 2009, 44: 1916-1926.
Voulgari K, et al: "Antifungal activity of non-starter lactic acid bacteria isolates from dairy products", Food Control, vol. 21, No. 2, Feb. 1, 2010.
Ju et al., "Review on the Function of Lactobacillus paracasei and application in food industry", China Dairy Industry, 37(8):48-50 (Dec. 2009), with English abstract attached.
Office action dated Sep. 16, 2014 issued in Chinese Application No. 201280028255.8, with English translation.
U.S. Appl. No. 14/390,231, filed Oct. 2, 2014, Hornbaek et al.
U.S. Appl. No. 14/390,238, filed Oct. 2, 2014, Hornbaek et al.
USPTO Corrected Notice of Allowability issued in U.S. Appl. No. 14/390,231 (U.S. Pat. No. 2015-0079057) dated Sep. 7, 2016.
USPTO Notice of Allowance issued in U.S. Appl. No. 14/390,231 (U.S. Pat. No. 2015-0079057) dated Jun. 20, 2016.
USPTO Restriction Requirement issued in U.S. Appl. No. 14/390,238 (U.S. Pat. No. 2015-0064152) dated Aug. 1, 2016.
International Preliminary Report on Patentability issued in application PCT/EP2012/056384, dated Oct. 8, 2013; 4 pages.
The State Intellectual Property Office of the People's Republic of China, First Office Action, Application 201380018783.X, dated Aug. 31, 2015 (with English translation); 21 pages.
USPTO Notice of Allowance issued in U.S. Appl. No. 14/390,231 (U.S. Pat. No. 2015-0079057), dated May 4, 2016; 10 pages.
USPTO Non-final Office Action issued in U.S. Appl. No. 14/390,231 (U.S. Pat. No. 2015-0079057), dated Sep. 22, 2015; 12 pages.
Office Action issued in co-pending U.S. Appl. No. 14/390,238, dated Sep. 5, 2017 (U.S. Pat. No. 2015/0064152).
Liptakova et al., "Characterisation of *Lactobacillus rhamnosus* VT1 and Its Effect on the Growth of *Candida maltose* YP1," *Czech J. Food Sci.*, vol. 25, No. 5, pp. 272-282 (2007).

* cited by examiner

SYNERGISTIC ANTIMICROBIAL EFFECT

CROSS-REFERENCE TO RELATED APPLICATIONS

This application is a national phase of International Application PCT/EP2012/056384, filed Apr. 9, 2012, which was published on Oct. 11, 2012, as WO 2012/136830, which claims the benefit of EP Application No. 11161609.0, filed Apr. 8, 2011. The respective contents of each of these applications are incorporated here by reference in their entirety.

FIELD OF THE INVENTION

The present invention is related to the field of bioprotection, in particular to an antimicrobial composition comprising a Lactobacillus rhamnosus strain and/or a Lactobacillus paracasei strain. Furthermore, the present invention concerns uses for such an antimicrobial composition, food, feed and pharmaceutical products comprising such an antimicrobial composition, a method of manufacturing such food, feed and pharmaceutical products and a method for reducing the content of unwanted microorganisms of such food, feed and pharmaceutical products.

BACKGROUND ART

Bioprotective cultures are used as alternatives to chemical preservatives in different food applications. In dairy products, contamination with yeast and molds may limit the shelf life of the dairy products. One product area experiencing significant yeast and mold contamination problems includes fresh cheeses.

Bioprotective solutions to overcome these problems have been developed by the dairy industry. Some of the most well-known and probably most commonly used antifungal bioprotective solutions on the market are the HOLDBAC™ YM-b and HOLDBAC™ YM-C cultures from Danisco that both contain combinations of subspecies of Propionibacteria and Lactobacillus.

The use of propionic acid bacteria together with lactic acid bacteria for inhibition of microorganisms has been disclosed in the patent applications US 2005/0095318 and WO 2004/041305.

Propionibacteria ssp. are believed to contribute to the antifungal activity mainly through the production of propionic acid but also through the production of acetic acid and other metabolites.

However, these species are rather costly to produce in an industrial scale and the production of propionic acid may cause unwanted sensory properties in the final dairy products.

Other antifungal bioprotective solutions on the market for dairy products include Lyofast LPRA from SACCO as well as Aroma-Prox®RP80 from BIOPROX. Both of these products contain combinations of Lactobacillus plantarum and Lactobacillus rhamnosus.

Tharmaraj and Shah (2009) describe the screening for bioprotective lactic acid bacterial candidates for cheese-based dips. All strains of Lactobacillus rhamnosus and Lactobacillus paracasei tested as single strains showed maximum inhibitory effect against yeasts and molds. However, no combinations of Lactobacillus rhamnosus and Lactobacillus paracasei were examined.

Thus, there is an industrial need to develop improved bioprotective solutions which omit Propionibacteria ssp. without compromising the antifungal effectiveness.

SUMMARY OF THE INVENTION

The present inventors have identified new strains of lactic acid bacteria which are significantly effective in inhibiting the growth of bacterial and fungal microorganisms that are known to occur as contaminants in milk and dairy products. The present inventors have further found that a certain group of lactic acid bacteria when combined with another group of lactic acid bacteria exhibit a significant synergistic antimicrobial effect. The antimicrobial effect of the two groups of bacteria combined, surprisingly, is greater than the sum of the individual effects of the two groups of bacteria.

Thus, a first aspect of the present invention relates to an antimicrobial composition comprising at least one strain of Lactobacillus rhamnosus and at least one strain of Lactobacillus paracasei. In a preferred embodiment, said antimicrobial composition comprises (a) at least one Lactobacillus strain selected from the group consisting of Lactobacillus rhamnosus CHCC12697 and Lactobacillus rhamnosus CHCC14226 and mutants thereof and (b) at least one Lactobacillus paracasei strain selected from the group consisting of Lactobacillus paracasei CHCC12777 and mutant strains thereof. In another preferred embodiment, the present invention provides an antimicrobial composition which comprises at least one strain selected from the group consisting of Lactobacillus rhamnosus strain CHCC12697, Lactobacillus rhamnosus strain CHCC14226, Lactobacillus paracasei strain CHCC12777, and mutant strains thereof, wherein the mutant strains are obtained by using the deposited strain as a starting material.

The compositions of the invention provide the advantage that unwanted microorganisms selected from fungi, bacteria and mixtures thereof, for example on food, feed and pharmaceutical products and in humans and animals, can be inhibited. The prevention and/or inhibition of the growth of fungi, such as yeasts and molds, is particularly envisaged. Therefore, in a preferred embodiment, the term "antimicrobial" is to be understood as "antifungal".

Therefore, a second aspect of the present invention is directed to use of one of the antimicrobial compositions of the first aspect in the preparation of a food, feed or pharmaceutical product.

A third aspect relates to the use of one of the antimicrobial compositions of the first aspect for inhibiting the growth of unwanted microorganisms selected from the group consisting of fungi, bacteria and mixtures thereof. In particular, the compositions of the invention shall be used for inhibiting and/or preventing the growth of fungi and bacteria which are commonly known contaminants in dairy industry processes, such as in milk fermentation processes.

A fourth aspect relates to the use of one of the antimicrobial compositions of the first aspect as a pharmaceutical product. The pharmaceutical product is preferably for use in treating an infection of a subject by bacteria or fungi, more preferably molds.

A fifth aspect relates to a food, feed or pharmaceutical product comprising one of the antimicrobial compositions according to the first aspect of the present invention.

A sixth aspect of the present invention is directed to a method for manufacturing the food, feed or pharmaceutical product according to the fifth aspect of the invention, the method comprising adding one of the antimicrobial compositions according to the first aspect of the present invention during the manufacture of the food, feed or pharmaceutical product. Where the method includes the addition of an antimicrobial composition which comprises a *Lactobacillus rhamnosus* strain in combination with a *Lactobacillus paracasei* strain, said composition is added such that the concentration of the at least one strain of *Lactobacillus rhamnosus* and the at least one strain of *Lactobacillus paracasei* is each at least $1 \times 10^6$ cfu/g, preferably $5 \times 10^6$ cfu/g, or each at least $1 \times 10^6$ cfu/ml, preferably $5 \times 10^6$ cfu/ml of the food, feed or pharmaceutical product, or each at least $1 \times 10^5$ cfu/cm$^2$, preferably $1 \times 10^7$ cfu/cm$^2$, of the surface of the food, feed or pharmaceutical product, and manufacturing parameters are controlled during the manufacturing such that the concentration of the at least one strain of *Lactobacillus rhamnosus* and the at least one strain of *Lactobacillus paracasei* increases or remains constant.

In a seventh aspect the present invention relates to a *Lactobacillus rhamnosus* CHCC12697 strain that was deposited with the German Collection of Microorganisms and Cell Cultures (DSMZ) under accession no. DSM24616, or a mutant strain thereof, wherein the mutant strain is obtained by using the deposited strain as starting material.

In an eighth aspect the present invention relates to a *Lactobacillus rhamnosus* CHCC14226 strain that was deposited with the German Collection of Microorganisms and Cell Cultures (DSMZ) under accession no. DSM24652, or a mutant strain thereof, wherein the mutant strain is obtained by using the deposited strain as starting material.

In a ninth aspect the present invention is directed to a *Lactobacillus paracasei* CHCC12777 strain that was deposited with the German Collection of Microorganisms and Cell Cultures (DSMZ) under accession no. DSM24651, or a mutant strain thereof, wherein the mutant strain is obtained by using the deposited strain as starting material.

DETAILED DESCRIPTION OF THE INVENTION

Definitions

Figure 1:
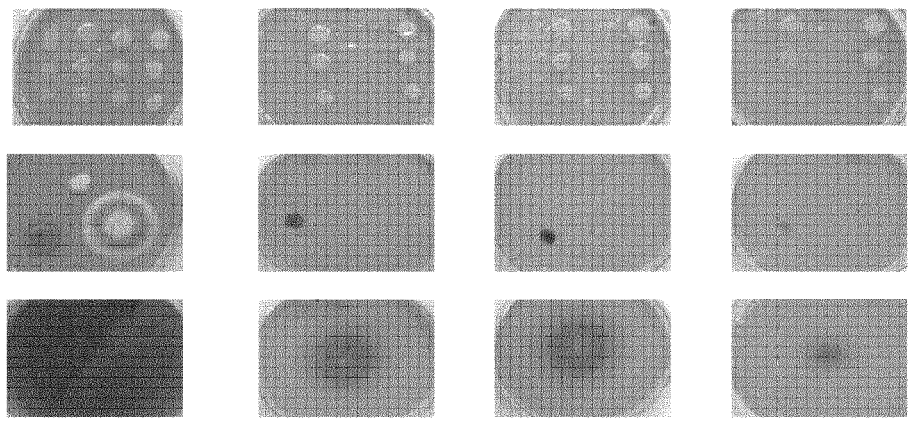
FIG. 1 shows growth of yeasts and molds on plates prepared from milk fermented with a starter culture alone (reference, first column), together with *Lb. rhamnosus* CHCC12697 (second column), together with *Lb. paracasei* CHCC12777 (third column) or together with a combination of *Lb. rhamnosus* CHCC12697 and *Lb. paracasei* CHCC12777 (fourth column). The target contaminants were added in the concentrations mentioned in the text from left to right: *K. marxianus, P. fermentans, Y. lipolytica* and *C. sake*, respectively, in the top row of plates. On the second row of plates *P. nalgiovense* was added at the top, *Cladiosporium* spp. added below to the left and *P. commune* added below to the right. On the last row of plates, *Mucor* ssp. was added alone. The plates had been incubated at 7±1° C. for 17 days.

As used herein, the term "lactic acid bacterium" designates a gram-positive, microaerophilic or anaerobic bacterium, which ferments sugars with the production of acids including lactic acid as the predominantly produced acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp. and *Enterococcus* spp. These are frequently used as food cultures alone or in combination with other lactic acid bacteria.

Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product or a cheese. Such lactic acid bacterial cultures are in general referred to as "starter cultures" or "starters".

The term "mesophile" herein refers to microorganisms that thrive best at moderate temperatures (15° C.-40° C.). The industrially most useful mesophilic bacteria include *Lactococcus* spp. and *Leuconostoc* spp. The term "mesophilic fermentation" herein refers to fermentation at a temperature between about 22° C. and about 35° C. The term "mesophilic fermented milk product" refers to fermented milk products prepared by mesophilic fermentation of a mesophilic starter culture and include such fermented milk products as buttermilk, sour milk, cultured milk, smetana, sour cream and fresh cheese, such as quark, tvarog and cream cheese.

The term "thermophile" herein refers to microorganisms that thrive best at temperatures above 43° C. The industrially most useful thermophilic bacteria include *Streptococcus* spp. and *Lactobacillus* spp. The term "thermophilic fermentation" herein refers to fermentation at a temperature above about 35° C., such as between about 35° C. to about 45° C. The term "thermophilic fermented milk product" refers to fermented milk products prepared by thermophilic fermentation of a thermophilic starter culture and include such fermented milk products as set-yoghurt, stirred-yoghurt and drinking yoghurt.

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk material that can be subjected to fermentation according to the method of the invention. Thus, useful milk substrates include, but are not limited to, solutions/suspensions of any milk or milk-like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of dairy products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid (such as a cheese) or liquid form (such as a fermented milk product).

The term "unwanted microorganisms" herein refers to microorganisms such as bacteria and fungi, such as yeasts, which are pathogenic and/or able to deteriorate food, feed or pharmaceutical products.

The terms "to inhibit" and "to be inhibiting" in relation to unwanted microorganisms mean for example that the growth or the number or the concentration of unwanted microorganisms, for example in food products and/or on the surface of food products comprising the antimicrobial composition, is lower than in food products and/or on the surface of food products which does not comprise such an antimicrobial composition.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties (e.g. regarding diacetyl production, viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood as one mutagenization step followed by a screening/selection step), but it is presently preferred that no more than 20, or no more than 10, or no more than 5 treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and Aspects of the Invention

The inventors have proceeded with extensive screening and research in order to provide an antimicrobial composition comprising one or a mixture of two different strains of lactic acid bacteria efficient against unwanted microorganisms, such as molds and yeasts.

The present inventors have screened among 200 candidates of *Lactobacillus plantarum*, *Lactobacillus paracasei* and *Lactobacillus rhamnosus* to find the most efficient single or two-strain combinations against a wide range of microorganisms, such as yeasts and molds.

Screenings were carried out in a model assay mimicking mesophilic fermented milk products as much as possible in milk-based media to which a relevant starter culture was added with or without bioprotective candidates and which was fermented under conditions relevant to mesophilic fermented milk products. Target organisms were isolated from mesophilic fermented milk products. Both the purified lactic acid bacteria from the HOLDBAC™ cultures from Danisco A/S, Denmark, as well as the complete HOLDBAC™ YM-B and HOLDBAC™ YM-C cultures containing both the lactic acid bacteria and propionic acid bacteria were used as bench mark.

Seventeen candidates among *Lactobacillus paracasei* and *Lactobacillus rhamnosus* were found generally to inhibit the 12 indicator fungi as well or better than the bench mark lactic acid bacteria when tested at 25° C. Thus, in a first aspect, the present invention relates to an antimicrobial composition comprising at least one strain of *Lactobacillus rhamnosus* or *Lactobacillus paracasei*.

Nine of the identified candidate strains also showed activities in the same range as the bench mark lactic acid bacteria when tested under chill conditions and particularly three strains were shown to be very efficient: *Lactobacillus paracasei* CHCC12777 with accession no. DSM24651, *Lactobacillus rhamnosus* CHCC12697 with accession no. DSM24616 and *Lactobacillus rhamnosus* CHCC14226 with accession no. DSM24652. These three strains were deposited with the German Collection of Microorganisms and Cell Cultures (DSMZ).

These single strains appeared to be better or comparable in effect against different yeasts, when tested in a so-called bottle-assay compared to HOLDBAC™ cultures. Thus, these single strains are highly suitable for use as antimicrobial agents. In a preferred aspect, the invention therefore provides an antimicrobial composition comprising at least one strain selected from the group consisting of:

*Lactobacillus rhamnosus* CHCC12697 that was deposited with the German Collection of Microorganisms and Cell Cultures (DSMZ) under accession no. DSM24616,

*Lactobacillus rhamnosus* CHCC14226 that was deposited with the German Collection of Microorganisms and Cell Cultures (DSMZ) under accession no. DSM24652,

*Lactobacillus paracasei* CHCC12777 that was deposited with the German Collection of Microorganisms and Cell Cultures (DSMZ) under accession no. DSM24651, and mutant strains thereof, wherein the mutant strains are obtained by using the deposited strain as a starting material.

In a particularly preferred embodiment, the antimicrobial composition of the invention comprises one of the above strains or a mutant thereof as the sole agent that exerts an antimicrobial activity.

Apart from the three strains mentioned above, the invention also pertains to mutants that have been derived from these strains, i.e. they have been obtained by using one of the deposited strains CHCC12777, CHCC12697 or CHCC14226 as a starting material. The mutant strain may be derived from one of these strains, e.g., by means of genetic engineering, radiation, UV light, chemical treatment and/or methods that induce changes in the genome. A mutant according to the invention will inhibit and/or prevent the growth of certain bacteria or fungi, preferably molds. It is preferred that the mutant has essentially at least 80% or more, at least 90% or more, at least 95% or more, or even up to 100% or more of the antimicrobial, e.g. antifungal, effect compared with its mother strain when determined, e.g., in an assay as described in Example 2 using one of the yeasts *K. marxianus, P. fermentas, Y. lipolytica* or *C. sake* as a contaminant.

The inhibiting effect of these strains against the unwanted microorganisms could be determined by storing the bottles at a suitable temperature during a suitable storage time as described in the Examples below.

In general, the suitable temperature at which this method should be performed depends on the temperature at which the specific food, feed or pharmaceutical product is normally stored and/or manufactured. The temperatures at which the bottles are usually stored are between 5° C. and 26° C., preferably the temperature is about 8° C.

The storage time at the temperature depends on the time during which the food, feed, or pharmaceutical product is normally stored (shelf life). The storage time usually is 7-28 days, preferably the storage time is about 21 days.

When tested in 2-strain combinations, it was unexpectedly found that the combinations of the most effective single strains were even better than either of the strains alone even when the total concentrations of cells which were added were equal for testing single strains and 2-strain combinations. The combinations of *Lactobacillus paracasei* CHCC12777 and *Lactobacillus rhamnosus* CHCC12697 or *Lactobacillus paracasei* CHCC12777 and *Lactobacillus rhamnosus* CHCC14226 seemed to be more efficient than the bench mark cultures HOLDBAC™ YM-B and HOLDBAC™ YM-C from Danisco, Denmark.

Accordingly, in a preferred embodiment the present invention relates to an antimicrobial composition comprising at least one strain of *Lactobacillus rhamnosus* and at least one strain of *Lactobacillus paracasei*, wherein the at least one strain of *Lactobacillus rhamnosus* is selected from the group consisting of *Lactobacillus rhamnosus* CHCC12697 with accession no. DSM24616, *Lactobacillus rhamnosus* CHCC14226 with accession no. DSM24652 and mutant strains thereof, wherein the mutant strains are obtained by using the deposited strain as starting material.

In another preferred embodiment the at least one strain of *Lactobacillus paracasei* is selected from the group consisting of *Lactobacillus paracasei* CHCC12777 with accession no. DSM24651 and mutant strains thereof, wherein the mutant strains are obtained by using the deposited strain as a starting material.

In further embodiments, the present invention relates to antimicrobial, and more preferably to antifungal compositions, comprising at least one strain of *Lactobacillus rhamnosus* and at least one strain of *Lactobacillus paracasei*, wherein
the at least one strain of *Lactobacillus rhamnosus* is selected from the group consisting of *Lactobacillus rhamnosus* CHCC12697 with accession no. DSM24616, *Lactobacillus rhamnosus* CHCC14226 with accession no. DSM24652 and mutant strains thereof, wherein the mutant strains are obtained by using the deposited strain as starting material; and
the at least one strain of *Lactobacillus paracasei* is selected from the group consisting of *Lactobacillus paracasei* CHCC12777 with accession no. DSM24651 and mutant strains thereof, wherein the mutant strains are obtained by using the deposited strain as a starting material.

An antimicrobial composition comprising at least *Lactobacillus rhamnosus* CHCC12697 and *Lactobacillus paracasei* CHCC12777 is particularly preferred. Likewise, an antimicrobial composition comprising at least *Lactobacillus rhamnosus* CHCC14226 and *Lactobacillus paracasei* CHCC12777 is particularly preferred according to the invention.

The antimicrobial composition typically comprises the bacteria in a concentrated form including frozen, dried or freeze-dried concentrates typically having a concentration of viable cells, which is in the range of $10^4$ to $10^{12}$ cfu (colony forming units) per gram of the composition including at least $10^4$ cfu per gram of the composition, such as at least $10^5$ cfu/g, e.g. at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g. Thus, the antimicrobial composition of the invention is preferably present in a frozen, dried or freeze-dried form, e.g. as a Direct Vat Set (DVS) culture. However, as used herein the antimicrobial composition may also be a liquid that is obtained after suspension of the frozen, dried or freeze-dried cell concentrates in a liquid medium such as water or PBS buffer. Where the antimicrobial composition of the invention is a suspension, the concentration of viable cells is in the range of $10^4$ to $10^{12}$ cfu (colony forming units) per ml of the composition including at least $10^4$ cfu per ml of the composition, such as at least $10^5$ cfu/ml, e.g. at least $10^6$ cfu/ml, such as at least $10^7$ cfu/ml, e.g. at least $10^8$ cfu/ml, such as at least $10^9$ cfu/ml, e.g. at least $10^{10}$ cfu/ml, such as at least $10^{11}$ cfu/ml.

The composition may additionally contain as further components cryoprotectants and/or conventional additives including nutrients such as yeast extracts, sugars and vitamins, e.g. vitamin A, C, D, K or vitamins of the vitamin B family. Suitable cryoprotectants that may be added to the compositions of the invention are components that improve the cold tolerance of the microorganisms, such as mannitol, sorbitol, sodium tripolyphosphate, xylitol, glycerol, raffinose, maltodextrin, erythritol, threitol, trehalose, glucose and fructose. Other additives to may include, e.g., carbohydrates, flavors, minerals, enzymes (e.g. rennet, lactase and/or phospholipase).

In antimicrobial compositions of the invention which comprise a *Lactobacillus rhamnosus* strain and a *Lactobacillus paracasei* strain, the ratio between the *Lactobacillus rhamnosus* strain and the *Lactobacillus paracasei* strain, e.g. the ratio of the concentration or number of *Lactobacillus rhamnosus* bacteria and the concentration or number of *Lactobacillus paracasei* bacteria, preferably amounts from 1:100 to 100:1, preferably 1:10 to 10:1.

The antimicrobial composition of the present invention may be used in connection with any food, feed and pharmaceutical product which is susceptible to microbial degradation and/or contamination with yeasts and molds. These include, but are not limited to fruits and vegetables including derived products, grain and grain-derived products, dairy products, meat, poultry, and seafood. In particularly preferred embodiments, the composition is used in connection with dairy product and/or meat and poultry. In a preferred embodiment, the compositions of the invention are for use as an additive in the preparation of dairy products, such as yoghurt, tvarog, sour cream, cream cheese and the like.

The antimicrobial composition according to the present invention may also be used for inhibiting unwanted microorganisms selected from the group consisting of fungi and bacteria and mixtures thereof. The compositions of the invention are particularly useful for inhibiting and/or preventing the growth of fungi and bacteria which are commonly known contaminants in dairy industry processes, such as in milk fermentation processes.

In a preferred embodiment the antimicrobial compositions of the invention are used against fungi, such as yeasts and molds. This means that the compositions are used for inhibiting and/or preventing the growth of fungi which cause contamination in dairy industry processes, in particular milk fermentation processes. The antimicrobial compositions of the present invention can be used, e.g., for inhibiting and/or preventing the growth of yeasts, such as yeasts of the genera *Klyveromyces* (e.g., *K. marxianus, K. lactis*), *Pichia* (e.g., *P. fermentans*), *Yarrowia* (e.g., *Y. lipolytica*), *Candida* (e.g., *C. sake*), and the like; or molds, such as molds from the genera *Penicillium* (e.g., *P. nalgiovense, P. commune, P. crustosum, P. brevicompactum, P. glabrum*), *Mucor* spp., *Cladiosporium* ssp., *Aspergillus* (e.g., *A. versicolor*), *Debaromyces* (e.g., *D. hansenii*), and the like. It is especially preferred to use the antimicrobial compositions of the invention to inhibit and/or prevent growth of the species *Klyveromyces marxianus, Yarrowia lipolytica, Penicillium nalgiovense, Cladiosporium* ssp., *Penicillium commune, Mucor* ssp., *Penicillium brevicompactum, Aspergillus versicolor, Penicillium crustosum, Kluyveromyces lactis*, and/or *Debaromyces hansenii*.

The antimicrobial composition according to the first aspect of the present invention may also be used as a pharmaceutical product for treating infections with pathogenic fungi, preferably pathogenic yeasts.

As said above, the present invention in one aspect is directed to a food, feed or pharmaceutical product comprising the antimicrobial compositions of the first aspect of the invention.

In a preferred embodiment such a food product is selected from the group consisting of fruits and fruit derived products, vegetable and vegetable derived products, grain and grain derived products, dairy products, meat, poultry and seafood and mixtures thereof.

In a more preferred embodiment the food product is a dairy product, preferably a mesophilic or a thermophilic fermented milk product, such as fresh cheese, yoghurt, sour cream or tvarog.

In another preferred embodiment the food product is meat or poultry.

In a preferred embodiment the pharmaceutical product is a product useful for administration of the antimicrobial composition according to a first aspect of the present invention to a human or an animal to inhibit pathogenic microorganisms and alleviating symptoms related to the pathogenic microorganisms. Examples of such symptoms include symptoms related to yeast infection. In such an embodiment, the pharmaceutical product may be a unit dosage form comprising the antimicrobial composition. Preferably, the unit dosage form is a capsule or a tablet. However, the unit dosage form may also be suitable for application to the mucosa or skin and, thus, be in the form of a paste, cream, ointment and the like.

Another aspect of the present invention relates to a method for manufacturing a food, feed or pharmaceutical product according to the fifth aspect of the present invention comprising adding the antimicrobial composition according to the first aspect of the invention during the manufacture of the food, feed, or pharmaceutical product.

In a preferred embodiment the concentration of the at least one strain of *Lactobacillus rhamnosus* or *Lactobacillus paracasei* is at least $1 \times 10^6$ cfu/g, preferably at least $5 \times 10^6$ cfu/g, most preferably at least $1 \times 10^8$ cfu/g, or at least $1 \times 10^6$ cfu/ml, preferably at least $5 \times 10^6$ cfu/ml, most preferably at least $1 \times 10^8$ cfu/ml, of the food, feed or pharmaceutical product, or at least $1 \times 10^5$ cfu/cm$^2$, preferably at least $1 \times 10^5$ cfu/cm$^2$, most preferably at least $1 \times 10^7$ cfu/cm$^2$, of the surface of the food, feed or pharmaceutical product.

Where the food, feed or pharmaceutical product is manufactured by addition of a composition comprising at least one strain of *Lactobacillus rhamnosus* and at least one strain of *Lactobacillus paracasei*, the concentration of the at least one strain of *Lactobacillus rhamnosus* and the at least one strain of *Lactobacillus paracasei* is each at least $1 \times 10^6$ cfu/g or each at least $1 \times 10^6$ cfu/ml of the food, feed or pharmaceutical product, or each at least $1 \times 10^5$ cfu/cm$^2$ of the surface of the food, feed or pharmaceutical product. Preferably, the concentration of the at least one strain of *Lactobacillus rhamnosus* and the at least one strain of *Lactobacillus paracasei* is each at least $5 \times 10^6$ cfu/g or each at least $5 \times 10^6$ cfu/ml of the food, feed or pharmaceutical product, or each at least $5 \times 10^5$ cfu/cm$^2$ of the surface of the food, feed or pharmaceutical product. In a further embodiment, the concentration of the at least one strain of *Lactobacillus rhamnosus* and the at least one strain of *Lactobacillus paracasei* is each at least $1 \times 10^8$ cfu/g or each at least $1 \times 10^8$ cfu/ml of the food, feed or pharmaceutical product, or each at least $1 \times 10^7$ cfu/cm$^2$ of the surface of the food, feed or pharmaceutical product.

In a preferred embodiment, the manufacturing parameters are controlled during the manufacturing such that the concentration of the at least one strain of *Lactobacillus rhamnosus* and the at least one strain of *Lactobacillus paracasei* increases or remains constant.

An antimicrobial composition according to the present invention is most readily used by mixing with and/or applying on a blendable food, feed or pharmaceutical product, but should also be effective to treat the surface of solid food products, or the interior of such products, e.g. by injection. In still other embodiments, the composition may be applied as a marinate, breading, seasoning rub, glaze, colorant mixture, and the like, the key criteria being that the antimicrobial composition be available to the surface that is subject to bacterial degradation and contamination with yeasts and molds. In still other embodiments, the composition may be indirectly placed into contact with the food surface by applying the composition to food packaging and thereafter applying the packaging to the food surface. The optimum amount to be used will depend on the composition of the particular food product to be treated and the method used for applying the composition to the food surface, but can be determined by simple experimentation.

In a much preferred embodiment the method comprises one or more fermentation steps and the antimicrobial composition may be added to the food, feed or pharmaceutical product prior to, during or after such one or more fermentation steps.

In an even more preferred embodiment the method comprises fermenting a milk substrate with a starter culture comprising at least one strain of the genera selected from *Lactobacillus, Streptococcus, Lactococcus* and *Leuconostoc*, such as at least one strain of *Lactobacillus bulgaricus* and at least one strain of *Streptococcus thermophilus* or such as at least one strain of *Lactococcus lactis* subsp. *lactis*, at least one strain of *Leuconostoc mesenteroides* subsp. *cremoris* and at least one strain of *Lactococcus lactis* subsp. *diacetylactis*.

The last aspects of the invention relate to the *Lactobacillus rhamnosus* CHCC12697 strain that was deposited with the German Collection of Microorganisms and Cell Cultures (DSMZ) under the accession no. DSM24616, or a mutant strain thereof, the *Lactobacillus rhamnosus* CHCC14226 strain that was deposited with the German Collection of Microorganisms and Cell Cultures (DSMZ) under the accession no. DSM24652, or a mutant strain thereof and the *Lactobacillus paracasei* CHCC12777 strain that was deposited with the German Collection of Microorganisms and Cell Cultures (DSMZ) under the accession no. DSM24651, or a mutant strain thereof, wherein the mutant strains are obtained by using the deposited strains as starting material.

It is clear for the skilled person that by using the deposited strain as starting material, the skilled reader can by conventional mutagenesis or re-isolation techniques routinely obtain further mutants or derivatives thereof that retain the herein described relevant features and advantages. Accordingly, the term "a mutant thereof" of the first aspect relates to mutant strains obtained by using the deposited strain as starting material.

Embodiments of the present invention are described below, by way of non-limiting examples.

EXAMPLES

Example 1

Semi-quantitative Determinations of the Inhibitory Effect of *Lb. paracasei* CHCC12777 and *Lb. rhamnosus* CHCC12697 Alone and in Combination Against Different Yeast and Mold Contaminants For the semi-quantitative examinations of the inhibitory effect of *Lb. paracasei* CHCC12777 and *Lb. rhamnosus* CHCC12697 alone and in combination, an agar-assay was used, resembling the manufacturing process and product of fresh cheese:

Full-fat (3.5% w/v) homogenized milk was heat-treated at 79±1° C. for 20 seconds and cooled immediately. A commercial starter culture (F-DVS CHN-19 obtainable from Chr. Hansen A/S, Denmark) was inoculated at 0.1 u/L, and the inoculated milk was distributed into 220 ml bottles. The different bottles were inoculated with *Lb. paracasei* CHCC12777 and/or *Lb. rhamnosus* CHCC12697 in total concentrations of $5 \times 10^6$ CFU/ml, and one bottle was used as a reference and only inoculated with the starter culture. Furthermore, 5% of a pH-indicator of bromcresol purple and bromcresol green was added to get an indication of the speed of acidification, and to obtain a blue/green colour of the media which would make subsequent growth of target yeasts and molds more easily detectable. All bottles were incubated in a water bath at 29±1° C. and fermented at these conditions until pH of 4.60±0.1 was reached. After fermentation, the bottles were immediately cooled on ice and vigorously shaken to break the coagulum. Then the fermented milk was warmed to a temperature of 40° C. and added to 40 ml of a 5% sterile agar solution that had been melted and cooled down to 60° C. This solution of fermented milk and agar was then poured into sterile Petri dishes and the plates were dried in a LAF bench for 30 min.

Selected yeasts and molds were spotted in concentrations of $10^4$, $10^3$ and $10^2$ CFU/spot, respectively for the yeasts *Klyveromyces marxianus*, *Pichia fermentans*, *Yarrowia lipolytica* and *Candida sake*. Fully outgrown spore suspensions were diluted 1000, 100, 10 or used undiluted for the molds *Penicillium nalgiovense*, *Mucor* ssp., *Penicillium commune* and *Cladiosporium* ssp., respectively. The plates were incubated at 7±1° C. and regularly examined for the growth of yeasts and molds.

Results of the agar-assay are presented in FIG. 1, showing that all of the tested yeasts and molds grew very well on the agar plates made from milk fermented only with the starter culture (reference). However, when *Lb. paracasei* CHCC12777 or *Lb. rhamnosus* CHCC12697 were present during milk fermentation the resulting plates prevented growth of *K. marxianus* and *Y. lipolytica* added in all concentrations. Furthermore, significant inhibition was observed for all the molds spotted onto the plates when *Lb. paracasei* CHCC12777 or *Lb. rhamnosus* CHCC12697 had been present during milk fermentation. Neither when *Lb. paracasei* CHCC12777 nor *Lb. rhamnosus* CHCC12697 were added as single strains did they seem to cause any inhibitory effect on the *P. fermentans* or *C. sake* strains. However, when *Lb. paracasei* CHCC12777 and *Lb. rhamnosus* CHCC12697 were both present during fermentation of the milk, growth inhibition of *P. fermentans* was observed when spotted in the lower concentrations of $10^2$ and $10^3$ CFU/spot, and the molds of *Cladiosporium* ssp. as well as *Mucor* ssp. were more inhibited than when either of the strains of *Lb. paracasei* CHCC12777 or *Lb. rhamnosus* CHCC12697 had been added alone. These results illustrate some synergistic antifungal effect of the two strains *Lb. paracasei* CHCC12777 and *Lb. rhamnosus* CHCC12697.

Example 2

Quantitative Determinations of the Inhibitory Effect of *Lb. paracasei* CHCC12777 and *Lb. rhamnosus* CHCC12697 Alone and in Combination Against *Yarrowia lipolytica*

For a quantitative examination of the inhibitory effect of *Lb. paracasei* CHCC12777 and *Lb. rhamnosus* CHCC12697 alone and in combination, an assay was used, resembling the manufacturing process and product of fresh cheese:

Full fat (3.5%, w/v) homogenised milk was heat-treated at 79±1° C. for 20 seconds and cooled immediately. A commercial starter culture (F-DVS CHN-19 obtainable from Chr. Hansen A/S, Denmark) was inoculated at 0.1 u/L, and the inoculated milk was distributed into 1 L bottles. The different bottles were inoculated with *Lb. paracasei* CHCC12777 and/or *Lb. rhamnosus* CHCC12697 in total concentrations of $5 \times 10^6$ CFU/ml, and one bottle was used as a reference and only inoculated with the starter culture. Furthermore, 2 bottles were inoculated either with HOLDBAC™ YM-B (50 DCU/100 L; Danisco A/S, Denmark) or HOLDBAC™ YM-C (20 DCU/100 L; Danisco A/S, Denmark) together with the CHN-19 starter culture. All bottles were incubated in a water bath at 29±1° C. and fermented at these conditions until pH of 4.65±0.05 was reached. After fermentation, the bottles were immediately cooled on ice and vigorously shaken to break the coagulum.

The content of each bottle was distributed into smaller plastic cups for inoculation of a *Yarrowia lipolytica* yeast strain previously isolated as a contaminant from a fresh cheese product. Two separate cups were inoculated in a volume of 1% (v/w) to achieve a final contamination level of *Y. lipolytica* in the fermented milk product of approx. $1 \times 10^2$ CFU/g. The plastic cups were sealed and stored at 8±1° C. The fermented milk products were regularly sampled for the *Y. lipolytica* contamination level by plating appropriate 10-fold dilutions made in saline peptone on Yeast Glucose Chloramphenicol (YGC) agar followed by aerobic incubation for 5 days at 25° C. Furthermore, the pH of the various fermented milk samples was regularly measured throughout storage.

Figure 2:
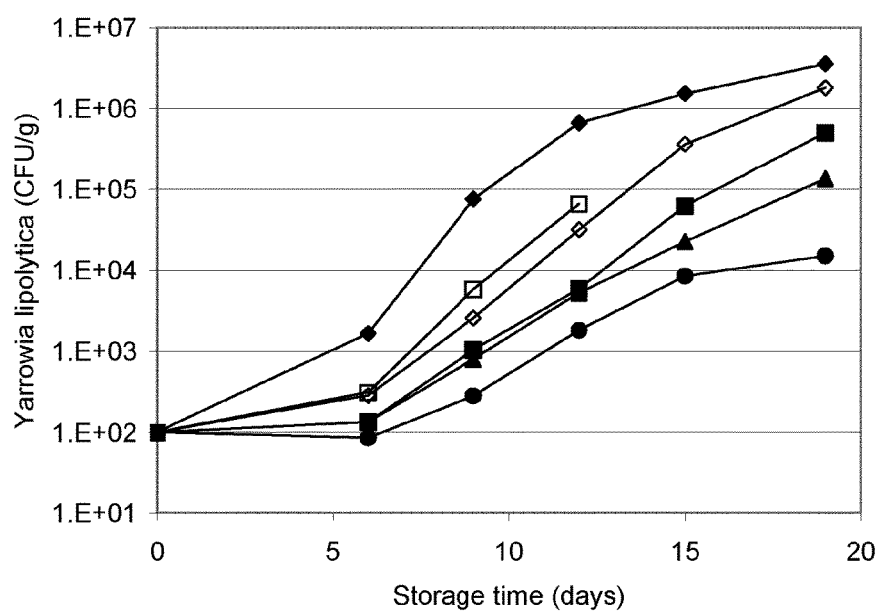
FIG. 2 depicts cell count of a *Yarrowia lipolytica* isolate added to full fat milk inoculated with the starter culture CHN-19 alone (closed diamond) or together with the following strains: HOLDBAC™ YM-B (open square), HOLDBAC™ YM-C (open diamond), *Lb. paracasei* CHCC12777 (closed square), *Lb. rhamnosus* CHCC12697 (closed triangle) or a combination of *Lb. paracasei* CHCC12777 and *Lb. rhamnosus* CHCC12697 (closed circle), all added before fermentation at 29±1° C. until a pH of 4.65±0.05 was reached.

As illustrated in FIG. 2, growth of *Y. lipolytica* was inhibited in the presence of both strains of *Lb. paracasei*

CHCC12777 and *Lb. rhamnosus* CHCC12697 when used as single strains together with the starter culture CHN-19 before fermentation. Both strains caused significantly higher inhibition than HOLDBAC™ YM-B and HOLDBAC™ YM-C. Furthermore, a synergistic inhibitory effect was found when *Lb. paracasei* CHCC12777 and *Lb. rhamnosus* CHCC12697 were used in combination compared to the inhibitory effect of each strain used alone. When used in combination, the strains *Lb. paracasei* CHCC12777 and *Lb. rhamnosus* CHCC12697 dramatically affected both the lag phase as well as the maximum cell count obtained for *Y. lipolytica* in the fermented milk product and this synergistic effect may contribute to an extension of shelf life for these type of products.

Example 3

Semi-quantitative Determinations of the Inhibitory Effect of *Lb. paracasei* CHCC12777 and *Lb. rhamnosus* CHCC14226 alone and in Combination Against Different Yeast and Mold Contaminants For the semi-quantitative examinations of the inhibitory effect of *Lb. paracasei* CHCC12777 and *Lb. rhamnosus* CHCC14226 alone and in combination, an agar-assay was used, resembling the manufacturing process and product of fresh cheese:

Full-fat (3.5% w/v) homogenized milk was heat-treated at 79±1° C. for 20 seconds and cooled immediately. A commercial starter culture (F-DVS CHN-19) was inoculated at 0.1 u/L, and the inoculated milk was distributed into 220 ml bottles. The different bottles were inoculated with *Lb. paracasei* CHCC12777 and/or *Lb. rhamnosus* CHCC14226 in total concentrations of $5\times10^6$ CFU/ml, and one bottle was used as a reference and only inoculated with the starter culture. Furthermore, 5% of a pH-indicator of bromcresol purple and bromcresol green was added to get an indication of the speed of acidification, and to obtain a blue/green colour of the media which would make subsequent growth of target yeasts and molds more easily detectable. All bottles were incubated in a water bath at 29±1° C. and fermented at these conditions until pH of 4.60±0.1 was reached. After fermentation, the bottles were immediately cooled on ice and vigorously shaken to break the coagulum. Then the fermented milk was warmed to a temperature of 40° C. and added to 40 ml of a 5% sterile agar solution that had been melted and cooled down to 60° C. This solution of fermented milk and agar was then poured into sterile Petri dishes and the plates were dried in a LAF bench for 30 min.

Selected yeasts and molds were spotted in concentrations of $10^4$, $10^3$ and $10^2$ CFU/spot, respectively for the yeasts *Klyveromyces marxianus, Pichia fermentans, Yarrowia lipolytica* and *Candida sake*. Fully outgrown spore suspensions were diluted 1000, 100, 10 or used undiluted for the molds *Penicillium nalgiovense, Mucor* ssp., *Penicillium commune* and *Cladiosporium* ssp., respectively. The plates were incubated at 7±1° C. and regularly examined for the growth of yeasts and molds.

Figure 3:
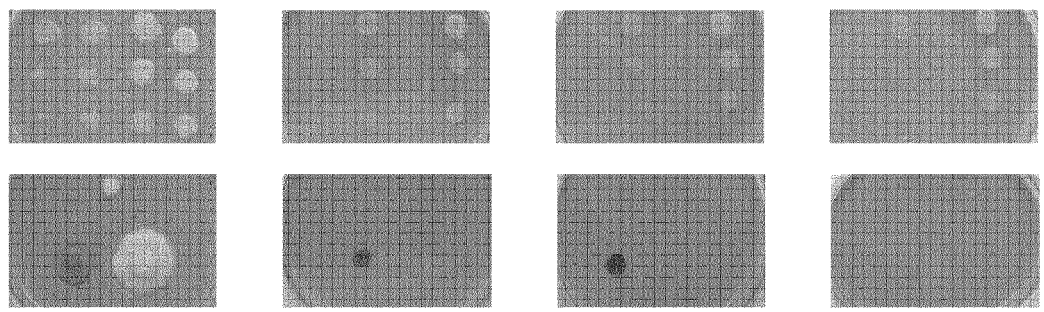
FIG. 3 shows growth of yeasts and molds on plates prepared from milk fermented with a starter culture alone (reference, first column), together with *Lb. rhamnosus* CHCC14226 (second column), together with *Lb. paracasei* CHCC12777 (third column) or together with a combination of *Lb. rhamnosus* CHCC14226 and *Lb. paracasei* CHCC12777 (fourth column). The target contaminants were added in the concentrations mentioned in the text from left to right: *K. marxianus, P. fermentans, Y. lipolytica* and *C. sake*, respectively, in the top row of plates. On the bottom row of plates *P. nalgiovense* was added at the top, *Cladiosporium* spp. added below to the left and *P. commune* added below to the right. The plates had been incubated at 7±1° C. for 15 days.

Results of the agar-assay are presented in FIG. 3, showing that all of the tested yeasts and molds grew very well on the agar plates made from milk fermented only with the starter culture (reference). However, when *Lb. paracasei* CHCC12777 was present during milk fermentation the resulting plates prevented growth of *K. marxianus* and *Y. lipolytica* added in all concentrations. For *Lb. rhamnosus* CHCC14226, the resulting plates also prevented growth of *K. marxianus* in all concentrations added, as well as the two lowest concentrations of *Y. lipolytica* added. When *Lb. paracasei* CHCC12777 or *Lb. rhamnosus* CHCC14226 were added as single strains, they also seemed to cause a slight inhibitory effect on the lower concentrations of *P. fermentans* added. However, when *Lb. paracasei* CHCC12777 and *Lb. rhamnosus* CHCC14226 were both present during fermentation of the milk, growth of *P. fermentans* was prevented when added in the lowest concentration of $10^2$ CFU/spot. For the molds, significant inhibition was observed when *Lb. paracasei* CHCC12777 or *Lb. rhamnosus* CHCC14226 were present during milk fermentation. When using the combination of *Lb. paracasei* CHCC12777 and *Lb. rhamnosus* CHCC14226 growth of *Cladiosporium* ssp. was more inhibited than when either of the strains of *Lb. paracasei* CHCC12777 or *Lb. rhamnosus* CHCC14226 had been added alone. These results illustrate some synergistic antifungal effect of the two strains *Lb. paracasei* CHCC12777 and *Lb. rhamnosus* CHCC14226.

Example 4

Quantitative Determinations of the Inhibitory Effect of *Lb. paracasei* CHCC12777 and *Lb. rhamnosus* CHCC14226 alone and in Combination Against *Klyveromyces marxianus*

For the examination of the inhibitory effect of *Lb. paracasei* CHCC12777 and *Lb. rhamnosus* CHCC14226 alone and in combination, an assay was used, resembling the manufacturing process and product of fresh cheese:

Full fat (3.5%, w/v) homogenised milk was heat-treated at 79±1° C. for 20 seconds and cooled immediately. A commercial starter culture (F-DVS CHN-19) was inoculated at 0.1 u/L, and the inoculated milk was distributed into 1 L bottles. The different bottles were inoculated with *Lb. paracasei* CHCC12777 and/or *Lb. rhamnosus* CHCC14226 in total concentrations of $5\times10^6$ CFU/ml, and one bottle was used as a reference and only inoculated with the starter culture. Furthermore, 2 bottles were inoculated either with HOLDBAC™ YM-B (50 DCU/100 L) or HOLDBAC™ YM-C (20 DCU/100 L) together with the CHN-19 starter culture. All bottles were incubated in a water bath at 29±1° C. and fermented at these conditions until pH of 4.65±0.05 was reached. After fermentation, the bottles were immediately cooled on ice and vigorously shaken to break the coagulum.

The content of each bottle was distributed into smaller plastic cups for inoculation of a *Klyveromyces marxianus* yeast strain previously isolated as a contaminant from a fresh cheese product. Two separate cups were inoculated in a volume of 1% (v/w) to achieve a final contamination level of *K. marxianus* in the fermented milk product of approx. $1\times10^2$ CFU/g. The plastic cups were sealed and stored at 8±1° C. The fermented milk products were regularly sampled for the *K. marxianus* contamination level by plating appropriate 10-fold dilutions made in saline peptone on Yeast Glucose Chloramphenicol (YGC) agar followed by aerobic incubation for 3-5 days at 25° C. Furthermore, the pH of the various fermented milk samples was regularly measured throughout storage.

Figure 4:
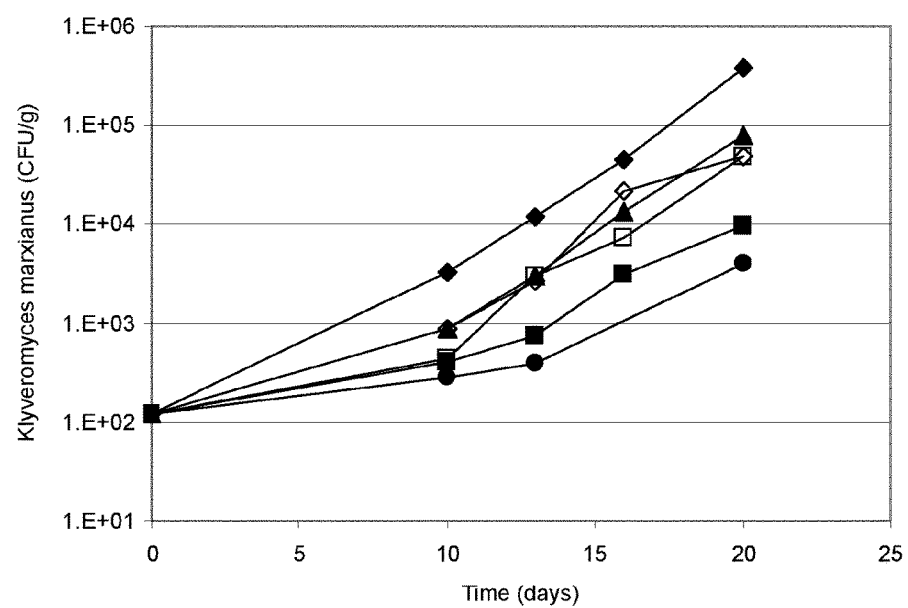
FIG. 4 depicts cell count of a *Klyveromyces marxianus* isolate added to full fat milk inoculated with the starter culture CHN-19 alone (closed diamond) or together with the following strains: HOLDBAC™ YM-B (open square), HOLDBAC™ YM-C (open diamond), *Lb. paracasei* CHCC12777 (closed square), *Lb. rhamnosus* CHCC14226 (closed triangle) or a combination of *Lb. paracasei* CHCC12777 and *Lb. rhamnosus* CHCC14226 (closed circle), all added before fermentation at 29±1° C. until a pH of 4.65±0.05 was reached.

As illustrated in FIG. 4, growth of *K. marxianus* was inhibited in the presence of both strains of *Lb. paracasei* CHCC12777 and *Lb. rhamnosus* CHCC14226 when used as single strains together with the starter culture CHN-19 before fermentation. As seen in example 2, *Lb. paracasei* CHCC12777 also caused significantly higher inhibition of *K. marxianus* than the HOLDBAC™ YM-B and HOLD- BAC™ YM-C cultures, whereas inhibition caused by *Lb. rhamnosus* CHCC14226 was found to be in the same level as the HOLDBAC™ cultures. A synergistic inhibitory effect was found when *Lb. paracasei* CHCC12777 and *Lb. rhamnosus* CHCC14226 were used in combination compared to the inhibitory effect of each strain used alone. When used in combination, the strains *Lb. paracasei* CHCC12777 and *Lb. rhamnosus* CHCC14226 resulted in slower growth of *K. marxianus* in the fermented milk product and may therefore contribute to an extension of shelf life for this type of products.

Example 5

Semi-quantitative Determinations of the Inhibitory Effect of *Lb. paracasei* CHCC14676 and *Lb. rhamnosus* CHCC5366 alone and in Combination Against Different Mold Contaminants For the semi-quantitative examinations of *Lb. paracasei* CHCC14676 and *Lb. rhamnosus* CHCC5366 alone and in combination, an agar-assay was used, resembling the manufacturing process and product of yoghurt:

Homogenized milk (1.5% fat w/v) was heat-treated at 95° C. for five minutes and cooled immediately. A commercial starter culture (F-DVS YC-350 obtainable from Chr. Hansen A/S, Denmark) was inoculated at 0.02%, and the milk was distributed to 220 ml bottles. The bottles were further inoculated with *Lb. paracasei* CHCC14676, *Lb. rhamnosus* CHCC5366 and a combination of the two strains, respectively, in total concentrations of $1\times10^7$ CFU/ml. One bottle without further inoculation than starter culture was used as reference. Furthermore, 5% of a pH-indicator of bromcresol purple and bromcresol green was added to all bottles to get an indication of the speed of acidification, and to obtain a blue/green color of the media which would make subsequent growth of target yeasts and molds more easily detectable. All bottles were incubated in a water bath at 43±1° C. and fermented at these conditions until pH of 4.60±0.1 was reached. After fermentation, the bottles were immediately cooled on ice and vigorously shaken to break the coagulum. Then the fermented milk was warmed to a temperature of 40° C. and added to 40 ml of a 5% sterile agar solution that had been melted and cooled down to 60° C. This solution was then poured into sterile Petri dishes and the plates were dried in a LAF bench for 30 min.

Fully outgrown spore suspensions in appropriate dilutions of the selected molds *Penicillium nalgiovese* (10×), *Penicillium commune* (100×), *Aspergillus versicolor* (100×) and *Penicillium crustosum* (100×) were spotted on the plates. The plates were incubated at 7° C. and examined for the growth of mold at suitable, regular intervals.

Figure 5:
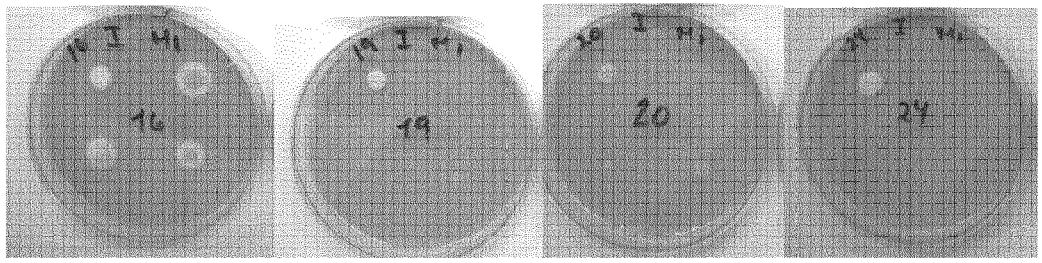
FIG. 5 shows growth of molds on plates prepared from milk fermented with a starter culture alone (reference, first picture), together with *Lb. paracasei* CHCC14676 (second picture), together with *Lb. rhamnosus* CHCC5366 (third picture) or together with a combination of *Lb. paracasei* CHCC14676 and *Lb. rhamnosus* CHCC5366 (fourth picture). The target contaminants were added in the concentrations mentioned in the text from top left to bottom right: *Penicillium nalgiovese, Penicillium commune, Aspergillus versicolor* and *Penicillium crustosum*, respectively. The plates had been incubated at 7±1° C. for 12 days.

Results of the agar-assay are presented in FIG. 5, showing that all of the tested molds grew very well on the agar plates from milk fermented only with the starter culture (reference). However, when *Lb. paracasei* CHCC14676 or *Lb. rhamnosus* CHCC5366 were present during milk fermentation, the resulting plates prevented growth of all molds. Furthermore, when *Lb. paracasei* CHCC14676 and *Lb. rhamnosus* CHCC5366 were present in combination during milk fermentation, significant inhibition was observed for *Penicillium commune*, *Aspergillus versicolor* and *Penicillium crustosum* spotted on the plates.

Example 6

Semi-quantitative Determinations of the Inhibitory Effect of *Lb. paracasei* CHCC14676 and *Lb. rhamnosus* CHCC14226 Alone and in Combination Against Different Mold Contaminants For the semi-quantitative examinations of *Lb. paracasei* CHCC14676 and *Lb. rhamnosus* CHCC14226 alone and in combination, an agar-assay was used, resembling the manufacturing process and product of yoghurt:

Homogenized milk (1.5% fat w/v) was heat-treated at 95° C. for five minutes and cooled immediately. A commercial starter culture (F-DVS Yoflex® Mild obtainable from Chr. Hansen A/S, Denmark) was inoculated at 0.02%, and the milk was distributed to 220 ml bottles. The bottles were further inoculated with *Lb. paracasei* CHCC14676, *Lb. rhamnosus* CHCC14226 and a combination of the two strains, respectively, in total concentrations of $1\times10^7$ CFU/ml. One bottle without further inoculation than starter culture was used as reference. Furthermore, 5% of a pH-indicator of bromcresol purple and bromcresol green was added to all bottles to get an indication of the speed of acidification, and to obtain a blue/green color of the media which would make subsequent growth of target yeasts and molds more easily detectable. All bottles were incubated in a water bath at 43±1° C. and fermented at these conditions until pH of 4.60±0.1 was reached. After fermentation, the bottles were immediately cooled on ice and vigorously shaken to break the coagulum. Then the fermented milk was warmed to a temperature of 40° C. and added to 40 ml of a 5% sterile agar solution that had been melted and cooled down to 60° C. This solution was then poured into sterile Petri dishes and the plates were dried in a LAF bench for 30 min.

Fully outgrown spore suspensions in appropriate dilutions of the selected molds *Penicillium nalgiovese* (10×), *Penicillium commune* (100×), *Aspergillus versicolor* (100×) and *Penicillium crustosum* (100×) were spotted on the plates. The plates were incubated at 7° C. and examined for the growth of mold at suitable, regular intervals.

Figure 6:
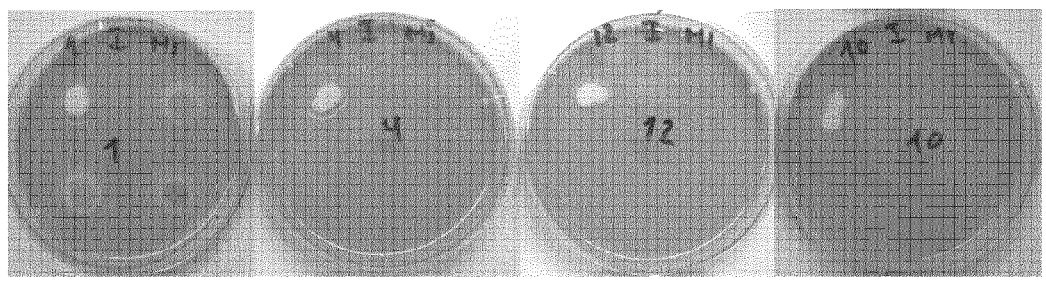
FIG. 6 shows growth of molds on plates prepared from milk fermented with a starter culture alone (reference, first picture), together with *Lb. paracasei* CHCC14676 (second picture), together with *Lb. rhamnosus* CHCC14226 (third picture) or together with a combination of *Lb. paracasei* CHCC14676 and *Lb. rhamnosus* CHCC14226 (fourth picture). The target contaminants were added in the concentrations mentioned in the text from top left to bottom right: *Penicillium nalgiovese, Penicillium commune, Aspergillus versicolor* and *Penicillium crustosum*, respectively. The plates had been incubated at 7±1° C. for 12 days.

Results of the agar-assay are presented in FIG. 6, showing that all of the tested molds grew very well on the agar plates from milk fermented only with the starter culture (reference). However, when *Lb. paracasei* CHCC14676 or *Lb. rhamnosus* CHCC14226 were present during milk fermentation, the resulting plates prevented growth of all molds. Furthermore, when *Lb. paracasei* CHCC14676 and *Lb. rhamnosus* CHCC14226 were present in combination during milk fermentation, significant inhibition was observed for *Penicillium commune*, *Aspergillus versicolor* and *Penicillium crustosum* spotted on the plates.

Example 7

Semi-quantitative Determinations of the Inhibitory Effect of *Lb. paracasei* CHCC12777 and *Lb. rhamnosus* CHCC14226 alone and in Combination Against Different Mold Contaminants For the semi-quantitative examinations of *Lb. paracasei* CHCC12777 and *Lb. rhamnosus* CHCC14226 alone and in combination, an agar-assay was used, resembling the manufacturing process and product of yoghurt:

Homogenized milk (1.5% fat w/v) was heat-treated at 95° C. for five minutes and cooled immediately. A commercial starter culture (F-DVS YC-350 obtainable from Chr. Hansen A/S, Denmark) was inoculated at 0.02%, and the milk was distributed to 220 ml bottles. The bottles were further inoculated with *Lb. paracasei* CHCC12777, *Lb. rhamnosus* CHCC14226 and a combination of the two strains, respectively, in total concentrations of $1\times10^7$ CFU/ml. One bottle without further inoculation than starter culture was used as reference. Furthermore, 5% of a pH-indicator of bromcresol purple and bromcresol green was added to all bottles to get an indication of the speed of acidification, and to obtain a blue/green color of the media which would make subsequent growth of target yeasts and molds more easily detectable. All bottles were incubated in a water bath at 43±1° C. and fermented at these conditions until pH of 4.60±0.1 was reached. After fermentation, the bottles were immediately cooled on ice and vigorously shaken to break the coagulum. Then the fermented milk was warmed to a temperature of 40° C. and added to 40 ml of a 5% sterile agar solution that had been melted and cooled down to 60° C. This solution was then poured into sterile Petri dishes and the plates were dried in a LAF bench for 30 min.

Fully outgrown spore suspensions in appropriate dilutions of the selected molds *Penicillium nalgiovese* (10×), *Penicillium commune* (100×), *Aspergillus versicolor* (100×) and *Penicillium crustosum* (100×) were spotted on the plates. The plates were incubated at 7° C. and examined for the growth of mold at suitable, regular intervals.

Figure 7:
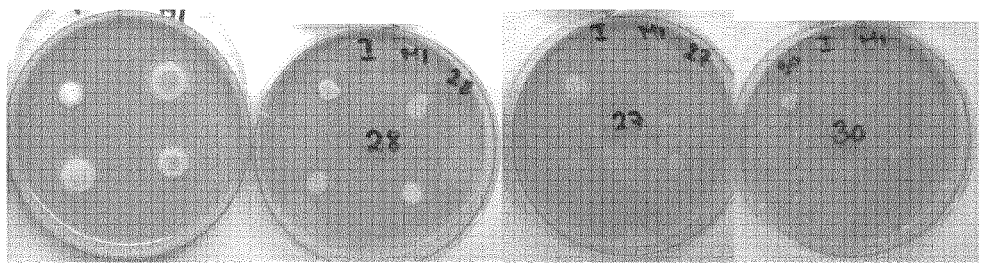
FIG. 7 shows growth of molds on plates prepared from milk fermented with a starter culture alone (reference, first picture), together with *Lb. paracasei* CHCC12777 (second picture), together with *Lb. rhamnosus* CHCC14226 (third picture) or together with a combination of *Lb. paracasei* CHCC12777 and *Lb. rhamnosus* CHCC14226 (fourth picture). The target contaminants were added in the concentrations mentioned in the text from top left to bottom right: *Penicillium nalgiovese, Penicillium commune, Aspergillus versicolor* and *Penicillium crustosum*, respectively. The plates had been incubated at 7±1° C. for 12 days.

Results of the agar-assay are presented in FIG. 7, showing that all of the tested molds grew very well on the agar plates from milk fermented only with the starter culture (reference). However, when *Lb. paracasei* CHCC12777 or *Lb. rhamnosus* CHCC14226 were present during milk fermentation, the resulting plates prevented growth of all molds. Furthermore, when *Lb. paracasei* CHCC12777 and *Lb. rhamnosus* CHCC14226 were present in combination during milk fermentation, significant inhibition was observed for all molds spotted on the plates.

Example 8

Challenge Study on Sour Cream with *Lactobacillus paracasei* CHCC12777

For the visual examination of the inhibitory effect of *Lactobacillus paracasei* strain CHCC12777 as single strain on the different molds *P. commune*, *A. versicolor*, *P. brevicompactum*, *P. crustosum* and *P. glabrum*, sour cream was prepared:

Pasteurized high fat milk was inoculated with a heterofermentative commercial starter culture (F-DVS DSG-2000 obtainable from Chr. Hansen A/S, Denmark) at 0.01%. The milk was further inoculated with HOLDBAC™ YM-B (10 DCU/100 L) or *Lactobacillus rhamnosus* strain CHCC12777 ($5\times10^6$ CFU/g) and one batch was used as reference and only inoculated with starter culture.

The milk was fermented at 28° C.±1° C. until pH of 4.6010.05 was reached and the sour cream was post treated. The sour cream was stirred and cooled to 20° C.±1° C. and stored at 7° C.±1° C.

One day after preparation of sour cream, different molds were inoculated as surface contaminants in duplicate cups of yoghurt with one spot on the surface of the yoghurt with a target of 100 spores/spot. Growth of the molds was assessed visually after storage for 45 days at 7° C.±1° C.

Figure 8:
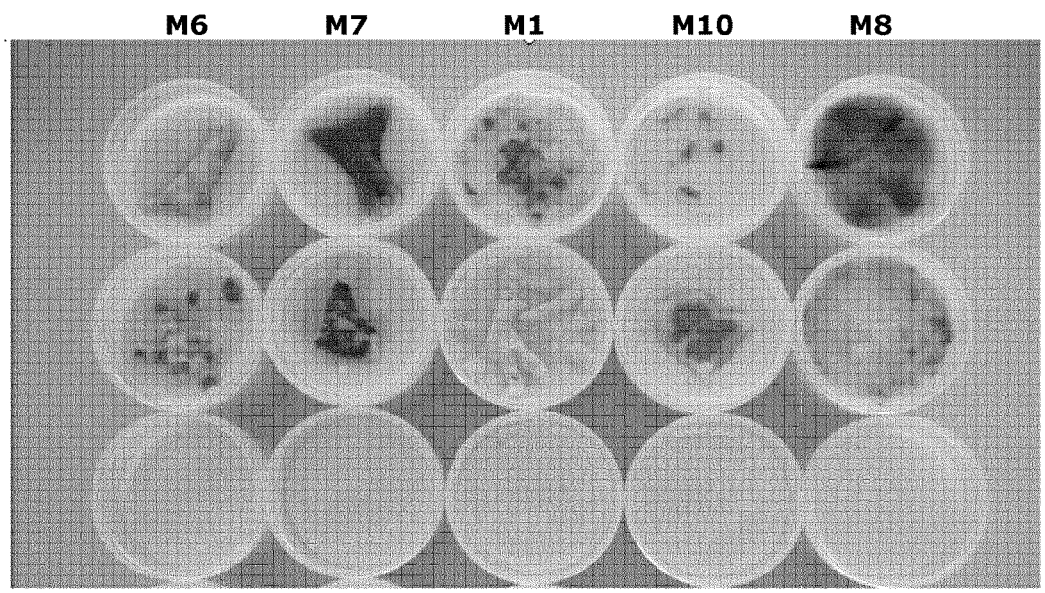
FIG. 8 shows the results of a challenge study on sour cream with *Lactobacillus paracasei* CHCC12777. It is demonstrated that *P. commune* (M6), *A. versicolor* (M7), *P. brevicompactum* (M1), *P. crustosum* (M10) and *P. glabrum* (M8) grow well on the sour cream made from milk fermented only with the starter culture (top row) or with the starter culture and the HOLDBAC™ YM-B culture (middle row). In contrast, when *Lactobacillus paracasei* CHCC12777 was present during milk fermentation (bottom row) the growth of all tested molds was inhibited.

The result of the sour cream test is presented in FIG. 8, showing that *P. commune* (M6), *A. versicolor* (M7), *P. brevicompactum* (M1), *P. crustosum* (M10) and *P. glabrum* (M8) grow well on the sour cream made from milk fermented only with the starter culture (top row) or with the starter culture and the HOLDBAC™ YM-B culture (middle row). In contrast, when *Lactobacillus paracasei* CHCC12777 was present during milk fermentation (bottom row) the growth of all tested molds was inhibited.

Example 9

Challenge Study on Tvarog with *Lactobacillus rhamnosus* CHCC12697

For the visual examination of the inhibitory effect of *Lactobacillus rhamnosus* strain CHCC12697 as single strain on *mucor* ssp., tvarog was prepared:

Pasteurized low fat milk was inoculated with a commercial starter culture (F-DVS CHN-19 obtainable from Chr. Hansen A/S, Denmark) at 0.01%. The milk was further inoculated with HOLDBAC™ YM-B (5 DCU/100 L) or *Lactobacillus rhamnosus* strain CHCC12697 ($5\times10^6$ CFU/g) and one batch was used as reference and only inoculated with starter culture.

The milk was fermented at 28° C.±1° C. until pH of 4.60±0.05 was reached. The scalding temperature was around 38-40° C. After draining the curd was pressed for 30 min. at 1 bar.

One day after preparation of tvarog, *Mucor* ssp. was inoculated as surface contaminant in duplicates by pipetting three spots on the surface of tvarog (100 g) with a target of 100 spores/spot. Growth of the mold was assessed visually after storage for 18 days at 7° C.±1° C.

Figure 9:
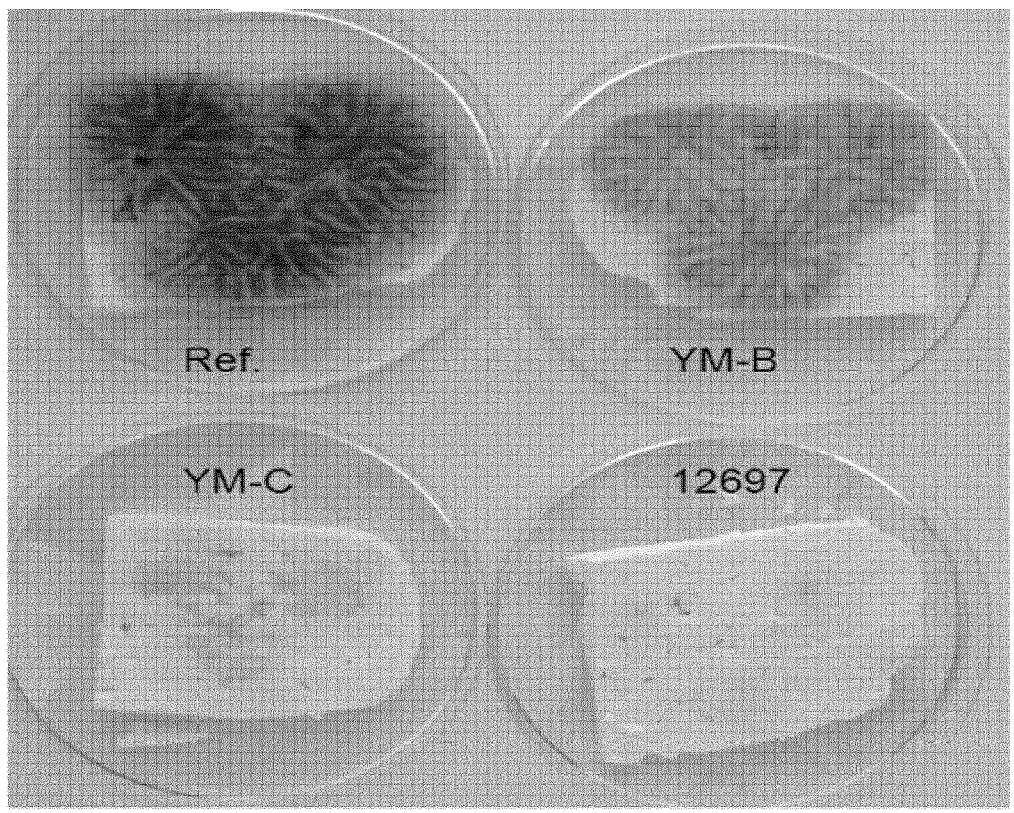
FIG. 9 shows a challenge study on tvarog with *Lactobacillus rhamnosus* CHCC12697. It is demonstrated that *Mucor* ssp. grows well on the tvarog made from milk fermented only with the starter culture CHN-19 (Ref.). The mold also grows well on tvarog made with milk fermented with the starter culture and the HOLDBAC™ YM-B culture and to a lesser extent in tvarog made with milk fermented with the starter culture and the HOLDBAC™ YM-C culture. However, when *Lactobacillus rhamnosus* strain CHCC12697 is present during fermentation of the milk, a significantly more prominent growth inhibition of *Mucor* ssp. is observed.

The result of the tvarog test is presented in FIG. 9, showing that *Mucor* ssp. grows well on the tvarog made from milk fermented only with the starter culture CHN-19 (Ref.). The mold also grows well on tvarog made with milk fermented with the starter culture and the HOLDBAC™ YM-B culture and to a lesser extent in tvarog made with milk fermented with the starter culture and the HOLDBAC™ YM-C culture. However, when *Lactobacillus rhamnosus* strain CHCC12697 is present during fermentation of the milk, a significantly more prominent growth inhibition of *Mucor* ssp. is observed.

Example 10

Challenge Study on Yoghurt with *Lactobacillus rhamnosus* CHCC14226

For the visual examination of the inhibitory effect of *Lactobacillus rhamnosus* strain CHCC14226 as single strains on the different molds, *P. brevicompactum*, *P. commune*, *A. versicolor* and *P. crustosum*, yoghurt with 1.5% fat was prepared:

Homogenized milk (1.5% fat) was heat-treated 95° C.±1° C. for 5 min. in 1 L bottles in a waterbath and cooled immediately. A commercial starter culture (F-DVS YF-L901 obtainable from Chr. Hansen A/S, Denmark) was inoculated at 0.02%. The milk was further inoculated with HOLDBAC™ YM-B (20 DCU/100 L) or *Lactobacillus rhamnosus* CHCC14226 ($1\times10^7$ CFU/ml) and one bottle was used as reference and only inoculated with starter culture.

The milk was fermented at 43° C.±1° C. until pH of 4.60±0.05 was reached. The resulting yoghurt was poured into cups (100 g) and stored at 7° C.±1° C.

One day after preparation of yoghurt different molds were inoculated as surface contaminants in duplicate cups of yoghurt with one spot on the surface of the yoghurt with a target of 100 spores/spot. Growth of the molds was assessed visually after storage for 45 days at 7° C.±1° C.

Figure 10:
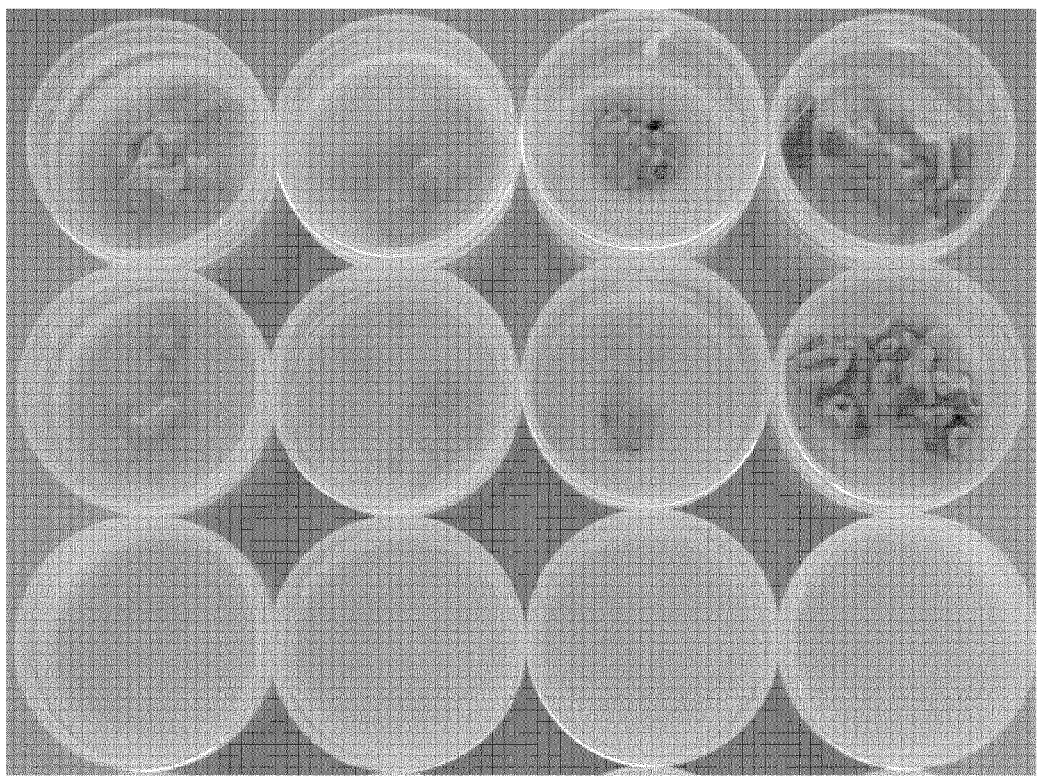
FIG. 10 shows a challenge study on yoghurt with *Lactobacillus rhamnosus* CHCC14226. *P. brevicompactum* (M1), *P. commune* (M6), *A. versicolor* (M7) and *P. crustosum* (M10) grow well on yoghurt made from milk fermented only with the starter culture YF-L901 (top row) or with the starter culture and the HOLDBAC™ YM-B culture (middle row). In contrast, when *Lactobacillus rhamnosus* CHCC14226 was present during milk fermentation (bottom row) the growth of all tested molds was inhibited.

The result of the yoghurt test is presented in FIG. 10, showing that *P. brevicompactum* (M1), *P. commune* (M6), *A. versicolor* (M7) and *P. crustosum* (M10) grow well on yoghurt made from milk fermented only with the starter culture YF-L901 (top row) or with the starter culture and the HOLDBAC™ YM-B culture (middle row). In contrast, when *Lactobacillus rhamnosus* CHCC14226 was present during milk fermentation (bottom row) the growth of all tested molds was inhibited.

Example 11

Quantitative Determinations of the Inhibitory Effect of *Lactobacillus paracasei* CHCC12777 Against *K. lactis* in Tvarog For a quantitative examination of the inhibitory effect of *Lactobacillus paracasei* strain CHCC12777 as single strain on *K. lactis*, tvarog was prepared:

Pasteurized low fat milk was inoculated with a commercial starter culture (F-DVS CHN-19 obtainable from Chr. Hansen A/S, Denmark) at 0.01%. The milk was further inoculated with HOLDBAC™ YM-B (20 DCU/100 L) or *Lactobacillus rhamnosus* strain CHCC12777 ($5\times10^5$ CFU/g) and one batch was used as reference and only inoculated with starter culture.

The milk was fermented at 28° C.±1° C. until pH of 4.60±0.05 was reached. The scalding temperature was around 38-40° C. After draining the curd was pressed for 30 min. at 1 bar.

The day after preparing the tvarog, sample blocks of tvarog of approx. 10 g were cut out and placed in stomacher bags. The blocks were subsequently inoculated in duplicate with 0.1 ml yeast inoculum at 10.000 CFU/ml by injecting the yeast inside the tvarog with a thin needle. The bags were wrapped around the tvarog and taped closed.

The samples were stored at 7° C.±1° C. and analyzed at suitable intervals for the *K. lactis* contamination level by plating 1 g of tvarog and further appropriate 1-fold dilutions made in saline peptone on Yeast Glucose Chloramphenicol (YGC) agar followed by aerobic incubation for 5 days at 25° C.

Figure 11:
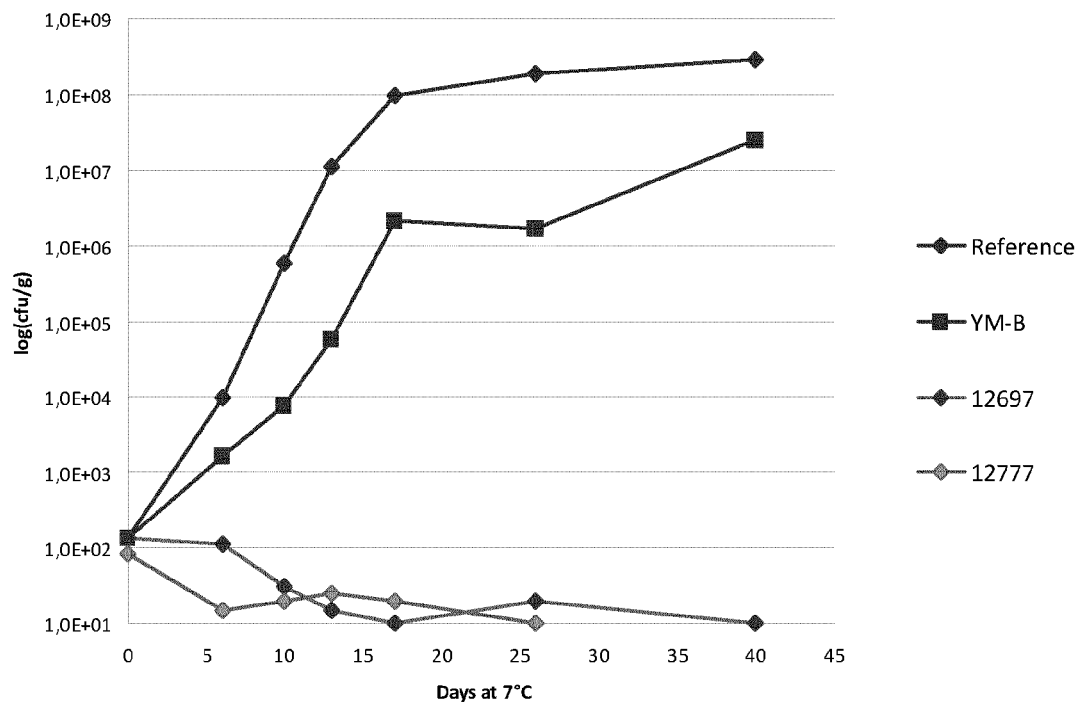
FIG. 11 shows the quantitative determination of the inhibitory effects of *Lactobacillus paracasei* CHCC12777 and *Lactobacillus rhamnosus* CHCC12697 against *K. lactis* in tvarog. It was demonstrated that growth of *K. lactis* was inhibited in the presence of *Lactobacillus paracasei* strain CHCC12777 and in the presence of *Lactobacillus rhamnosus* strain CHCC12697 when inoculated together with the starter culture CHN-19 before fermentation. Both strains, the *Lactobacillus paracasei* strain CHCC12777 and the *Lactobacillus rhamnosus* strain CHCC12697, caused significantly higher inhibition than the commercial culture, HOLDBAC™ YM-B.

As illustrated in FIG. 11, growth of *K. lactis* was inhibited in the presence of *Lactobacillus paracasei* strain CHCC12777 when inoculated together with the starter culture CHN-19 before fermentation. The *Lactobacillus paracasei* strain CHCC12777 caused significantly higher inhibition than the commercial culture, HOLDBAC™ YM-B.

Example 12

Quantitative Determinations of the Inhibitory Effect of *Lactobacillus rhamnosus* CHCC12697 Against *K. lactis* in Tvarog For a quantitative examination of the inhibitory effect of *Lactobacillus rhamnosus* CHCC12697 as single strain on *K. lactis*, tvarog was prepared:

Pasteurized low fat milk was inoculated with a commercial starter culture (F-DVS CHN-19 obtainable from Chr. Hansen A/S, Denmark) at 0.01%. The milk was further inoculated with HOLDBAC™ YM-B (5 DCU/100 L) or *Lactobacillus rhamnosus* strain CHCC12697 ($5\times10^6$ CFU/g) and one batch was used as reference and only inoculated with starter culture.

The milk was fermented at 28° C.±1° C. until pH of 4.60±0.05 was reached. The scalding temperature was around 38-40° C. After draining the curd was pressed for 30 min. at 1 bar.

The day after preparing the tvarog, sample blocks of tvarog of approx. 10 g were cut out and placed in stomacher bags. The blocks were subsequently inoculated in duplicate with 0.1 ml yeast inoculum at 10.000 cfu/ml by injecting the yeast inside the tvarog with a thin needle. The bags were wrapped around the tvarog and taped closed.

The samples were stored at 7° C.±1° C. and analyzed at suitable intervals for the *K. lactis* contamination level by plating 1 g of tvarog and further appropriate 1-fold dilutions made in saline peptone on Yeast Glucose Chloramphenicol (YGC) agar followed by aerobic incubation for 5 days at 25° C.

As illustrated in FIG. 11, growth of *K. lactis* was inhibited in the presence of *Lactobacillus rhamnosus* strain CHCC12697 when inoculated together with the starter culture CHN-19 before fermentation. The strain caused significantly higher inhibition than the commercial culture, HOLDBAC™ YM-B.

Example 13

Quantitative Determinations of the Inhibitory Effect of *Lactobacillus rhamnosus* CHCC14226 Against *Debaromyces hansenii* in Yoghurt For a quantitative examination of the inhibitory effect of *Lactobacillus rhamnosus* CHCC14226 as single strain on *D. hansenii*, yoghurt was prepared as follows:

Homogenized milk (1.5% fat) was heat-treated 95° C.±1° C. for 5 min. in 1 L bottles in a water bath and cooled immediately. A commercial starter culture (F-DVS YF-L901 obtainable from Chr. Hansen A/S, Denmark) was inoculated at 0.02%. The milk was further inoculated with HOLDBAC™ YM-B (20 DCU/100 L) or *Lactobacillus rhamnosus* CHCC14226 ($1\times10^7$ CFU/g) and one bottle was used as reference and only inoculated with starter culture.

The milk was fermented at 43° C.±1° C. until pH of 4.60±0.1 was reached. The resulting yoghurt was poured into cups (100 g) and stored at 7° C.±1° C.

The day after preparing the yoghurt, the cups were inoculated in duplicate with 1.00 ml/cup of yeast at a target of 20 CFU/g. The yeast was equally dispersed in the yoghurt. The cups were stored under lid at 7° C.±1° C. and analyzed at suitable intervals for the *D. hansenii* contamination level by plating 1 ml of yoghurt and further appropriate 1-fold dilutions made in saline peptone on Yeast Glucose Chloramphenicol (YGC) agar followed by aerobic incubation for 5 days at 25° C.

Figure 12:
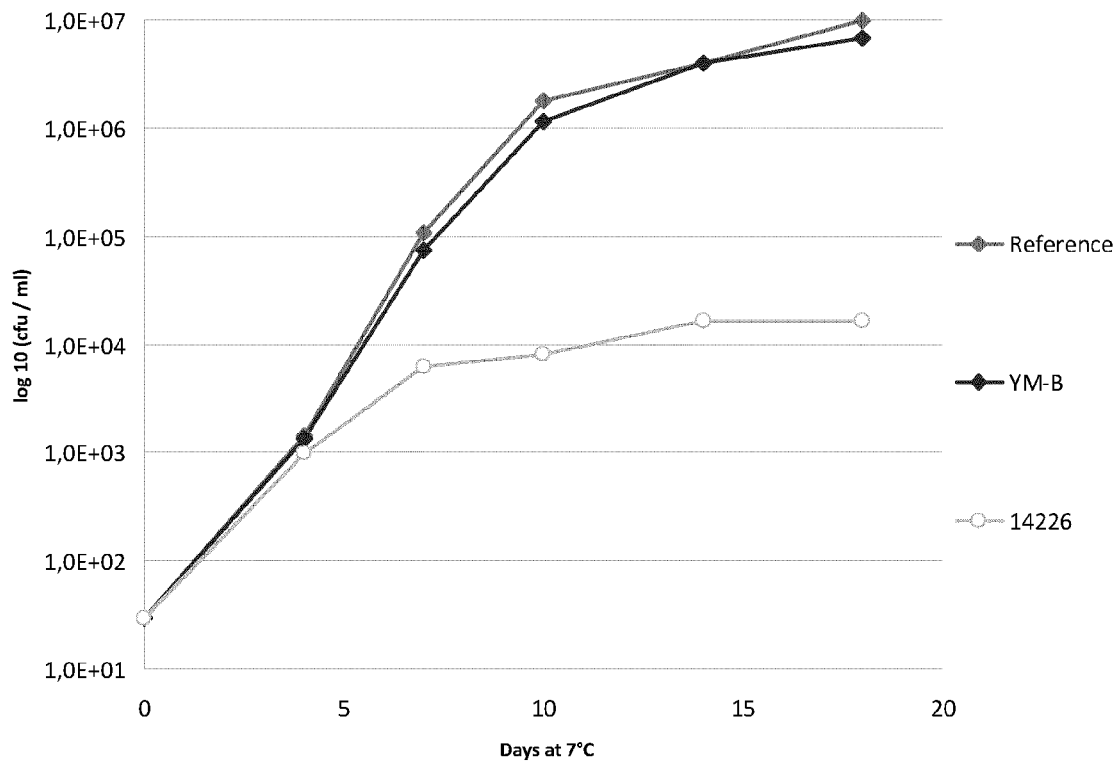
FIG. 12 shows the quantitative determination of the inhibitory effect of *Lactobacillus rhamnosus* CHCC14226 against *Debaromyces hansenii* in yoghurt. The growth of *D. hansenii* was inhibited in the presence of *Lactobacillus rhamnosus* strain CHCC14226 when inoculated together with the starter culture YF-L901 before fermentation. The strain caused significantly higher inhibition than the commercial culture, HOLDBAC™ YM-B.

As illustrated in FIG. 12, growth of *D. hansenii* was inhibited in the presence of *Lactobacillus rhamnosus* strain CHCC14226 when inoculated together with the starter culture YF-L901 before fermentation. The strain caused significantly higher inhibition than the commercial culture, HOLDBAC™ YM-B.

Deposits and Expert Solution

The applicant requests that a sample of the deposited micro-organisms stated below may only be made available to an expert, until the date on which the patent is granted.

The *Lactobacillus rhamnosus* strain CHCC12697 was deposited 2011 Mar. 1 at German Collection of Microorganisms and Cell Cultures (Deutsche Sammlung von Mikroorganismen und Zellkulturen GmbH; DSMZ), Inhoffenstr. 7B, D-38124 Braunschweig and given the accession No.: DSM24616.

The *Lactobacillus rhamnosus* strain CHCC14226 was deposited 2011 Mar. 15 at German Collection of Microorganisms and Cell Cultures (Deutsche Sammlung von Mikroorganismen und Zellkulturen GmbH; DSMZ), Inhoffenstr. 7B, D-38124 Braunschweig and given the accession No.: DSM24652.

The *Lactobacillus paracasei* strain CHCC12777 was deposited 2011 Mar. 15 at German Collection of Microorganisms and Cell Cultures (Deutsche Sammlung von Mikroorganismen and Zellkulturen GmbH; DSMZ), Inhoffenstr. 7B, D-38124 Braunschweig and given the accession No.: DSM24651.

The deposits were made according to the Budapest treaty on the international recognition of the deposit of microorganisms for the purposes of patent procedure.

REFERENCES

US 2005/0095318 (Schwenninger et al.)
WO 2004/041305 (Valio Ltd)
Tharmaraj, N. & Shah, N. P. (2009) Antimicrobial effects of probiotic bacteria against selected species of yeasts and molds in cheese-based dips. *International Journal of Food Science & Technology*. 44: 1916-1926.

The invention claimed is:

1. An antimicrobial composition comprising
at least one strain of *Lactobacillus rhamnosus* with antimicrobial properties selected from *Lactobacillus rhamnosus* CHCC12697 deposited with the German Collection of Microorganisms and Cell Cultures (DSMZ) under Accession No. DSM24616, *Lactobacillus rhamnosus* CHCC14226 deposited with the DSMZ under Accession No. DSM24652, and mutant strains of either that exhibit antimicrobial properties, and
at least one strain of *Lactobacillus paracasei* selected from *Lactobacillus paracasei* CHCC12777 deposited with the DSMZ under Accession No. DSM24651 and mutant strains thereof that exhibit antimicrobial properties,
wherein the composition comprises at least $1 \times 10^6$ cfu/g of the *Lactobacillus rhamnosus* strain(s) and at least $1 \times 10^6$ cfu/g of the *Lactobacillus paracasei* strain(s), wherein the ratio of *Lactobacillus rhamnosus* strain(s) to *Lactobacillus paracasei* strain(s) is from 1:100 to 100:1, and
wherein the composition has improved antimicrobial properties as compared to a comparison composition with the same total amount of the *Lactobacillus* bacteria but only one of the *Lactobacillus rhamnosus* strain(s) or the *Lactobacillus paracasei* strain(s).

2. A food, feed or pharmaceutical product comprising the antimicrobial composition according to claim 1.

3. A food product according to claim 2, wherein the food product is selected from the group consisting of fruits and fruit-derived products, vegetables and vegetable-derived products, grain and grain-derived products, dairy products, meat, poultry, seafood, and mixtures of two or more thereof.

4. A pharmaceutical product according to claim 2, wherein the pharmaceutical product is a unit dosage form comprising said antimicrobial composition.

5. A method for manufacturing a food, feed or pharmaceutical product according to claim 2, comprising adding said antimicrobial composition to a food, feed or pharmaceutical product.

6. The method according to claim 5, comprising:
(a) adding said antimicrobial composition during the manufacture of the food, feed or pharmaceutical product such that the concentration of the at least one strain of *Lactobacillus rhamnosus* and the at least one strain of *Lactobacillus paracasei* is each at least $1 \times 10^6$ cfu/g or at least $1 \times 10^6$ cfu/ml of the food, feed or pharmaceutical product, or at least $1 \times 10^5$ cfu/cm$^2$ of the surface of the food, feed or pharmaceutical product; and then
(b) controlling the manufacturing parameters during the manufacturing such that the concentration of the at least one strain of *Lactobacillus rhamnosus* and the at least one strain of *Lactobacillus paracasei* increases or remains constant.

7. The method according to claim 5, wherein the method comprises one or more fermentation steps.

8. A pharmaceutical product comprising the composition according to claim 1.

9. The antimicrobial composition of claim 1, wherein the composition comprises *Lactobacillus rhamnosus* CHCC12697 deposited with the DSMZ under Accession No. DSM24616.

10. The antimicrobial composition of claim 1, wherein the composition comprises *Lactobacillus rhamnosus* CHCC14226 deposited with the DSMZ under Accession No. DSM24652.

11. The antimicrobial composition of claim 1, wherein the composition comprises *Lactobacillus paracasei* CHCC12777 deposited with the DSMZ under Accession No. DSM24651.

12. The antimicrobial composition of claim 1, wherein the composition comprises a mutant strain obtained by using *L. rhamnosus* CHCC12697 deposited with the DSMZ under Accession No. DSM24616 or *L. rhamnosus* CHCC14226 deposited with the DSMZ under Accession No. DSM24652 as a starting material.

13. The antimicrobial composition of claim 1, wherein the composition comprises a *L. paracasei* mutant strain obtained by using *L. paracasei* CHCC12777 deposited with the DSMZ under Accession No. DSM24651 as a starting material.

14. The antimicrobial composition of claim 1, wherein the composition comprises an *L. rhamnosus* strain selected from CHCC12697 deposited with the DSMZ under Accession No. DSM24616 and CHCC14226 deposited with the DSMZ under Accession No. DSM24652, and comprises *L. paracasei* strain CHCC12777 deposited with the DSMZ under Accession No. DSM24651.

15. The antimicrobial composition of claim 1, wherein the ratio of *Lactobacillus rhamnosus* strain(s) to *Lactobacillus paracasei* strain(s) is from 1:10 to 10:1.

* * * * *